United States Patent
Adams et al.

(10) Patent No.: US 8,617,847 B2
(45) Date of Patent: Dec. 31, 2013

(54) NUCLEIC ACIDS ENCODING ANTIBODY MOLECULES WHICH BIND IL-17A AND IL-17F

(71) Applicant: UCB Pharma S.A., Brussels (BE)

(72) Inventors: Ralph Adams, Berkshire (GB); Andrew George Popplewell, Berkshire (GB); Stephen Edward Rapecki, Berkshire (GB)

(73) Assignee: UCB Pharma S.A., Brussels (BE)

( * ) Notice: Subject to any disclaimer, the term of this patent is extended or adjusted under 35 U.S.C. 154(b) by 0 days.

(21) Appl. No.: 13/632,702

(22) Filed: Oct. 1, 2012

(65) Prior Publication Data
US 2013/0102030 A1    Apr. 25, 2013

Related U.S. Application Data

(62) Division of application No. 12/446,143, filed as application No. PCT/GB2007/003983 on Oct. 18, 2007, now Pat. No. 8,303,953.

(30) Foreign Application Priority Data
Oct. 18, 2006    (GB) .................................. 0620729.4

(51) Int. Cl.
*C12P 21/08*    (2006.01)

(52) U.S. Cl.
USPC ................... 435/69.6; 536/23.53; 435/320.1; 435/325; 435/6.1; 530/388.23; 530/351

(58) Field of Classification Search
None
See application file for complete search history.

*Primary Examiner* — Dong Jiang
(74) *Attorney, Agent, or Firm* — McDonnell Boehnen Hulbert & Berghoff LLP

(57) ABSTRACT

The invention relates to antibody molecules having specificity for antigenic determinants of both IL-17A and IL-17F, therapeutic uses of the antibody molecules and methods for producing said antibody molecules.

17 Claims, 4 Drawing Sheets

Figure 1

Figure 2A:
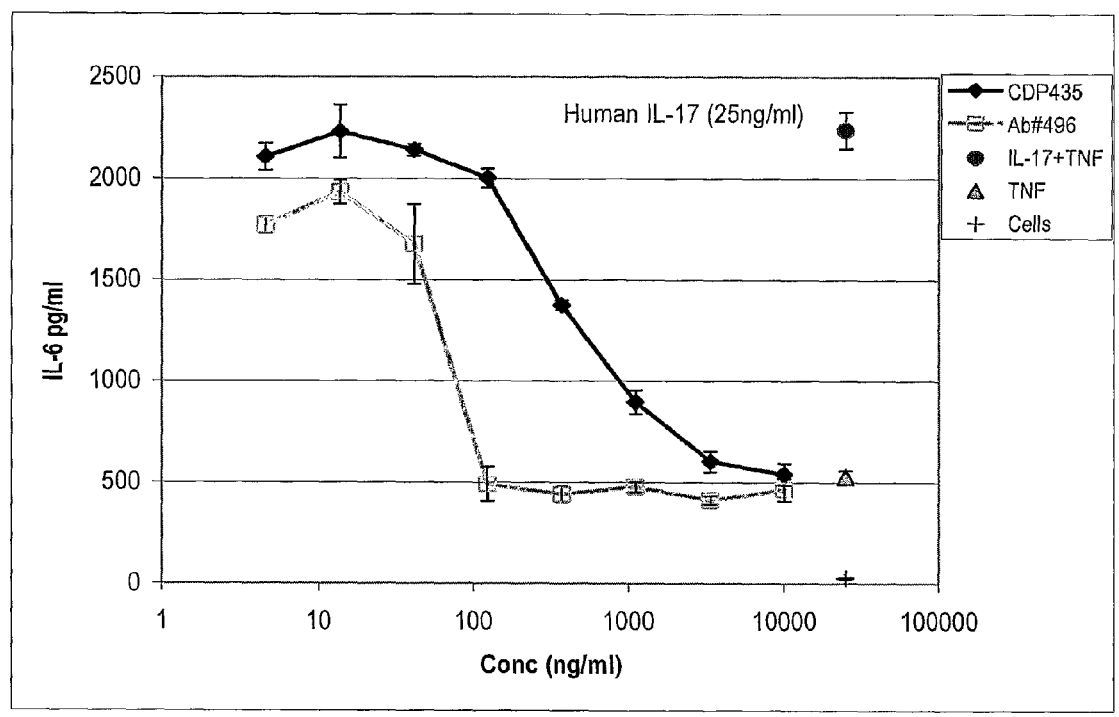

(a) Light Chain variable region of antibody CA028_496 (SEQ ID NO:7)
AIQLTQSPSSLSASVGDRVTITCRADESVTTLMHWYQQKPGKAPKLLIYLVSNRESGVPSRF
SGSGSGTDFTLTISSLQPEDFATYYCQQTWSDPWTFGQGTKVEIKR (b) Heavy Chain variable region of antibody CA028_496 (SEQ ID NO:9)
EVQLVESGGGLVQPGGSLRLSCAASGFTFSDYNMAWVRQAPGKGLEWVATITYEGRNTYYRD
SVKGRFTISRDNAKNSLYLQMNSLRAEDTAVYYCASPPQYYEGSIYRLWFAHWGQGTLVTVS
S (c)

| | |
|---|---|
| CDRH1: | GFTFSDYNMA (SEQ ID NO:1) |
| CDRH2: | TITYEGRNTYYRDSVKG (SEQ ID NO:2) |
| CDRH3: | PPQYYEGSIYRLWFAH (SEQ ID NO:3) |
| CDRL1: | RADESVTTLMH (SEQ ID NO:4) |
| CDRL2: | LVSNRES (SEQ ID NO:5) |
| CDRL3: | QQTWSDPWT (SEQ ID NO:6) |

(d) Light chain of antibody CA028_496 (SEQ ID NO:11)
AIQLTQSPSSLSASVGDRVTITCRADESVTTLMHWYQQKPGKAPKLLIYLVSNRESGVPSRF
SGSGSGTDFTLTISSLQPEDFATYYCQQTWSDPWTFGQGTKVEIKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGEC (e) Heavy chain of antibody CA028_496 (SEQ ID NO:15)
EVQLVESGGGLVQPGGSLRLSCAASGFTFSDYNMAWVRQAPGKGLEWVATITYEGRNTYYRD
SVKGRFTISRDNAKNSLYLQMNSLRAEDTAVYYCASPPQYYEGSIYRLWFAHWGQGTLVTVS
SASTKGPSVFPLAPCSRSTSESTAALGCLVKDYFPEPVTVSWNSGALTSGVHTFPAVLQSSG
LYSLSSVVTVPSSSLGTKTYTCNVDHKPSNTKVDKRVESKYGPPCPPCPAPEFLGGPSVFLF
PPKPKDTLMISRTPEVTCVVVDVSQEDPEVQFNWYVDGVEVHNAKTKPREEQFNSTYRVVSV
LTVLHQDWLNGKEYKCKVSNKGLPSSIEKTISKAKGQPREPQVYTLPPSQEEMTKNQVSLTC
LVKGFYPSDIAVEWESNGQPENNYKTTPPVLDSDGSFFLYSRLTVDKSRWQEGNVFSCSVMH
EALHNHYTQKSLSLSLGK (f) DNA encoding light chain of antibody CA028_496 including signal sequence (SEQ ID NO:14)
atgtcagttcccacacaggtgctgggcctgcttctgttgtggctcaccgatgctaggtgtgc
catccagctgacccagagcccttcctctctcagcgccagtgtcggagacagagtgactatta
cctgcagggctgacgaaagcgtgaccacattgatgcactggtaccaacagaagcctggcaaa
gcccccaagctcctgatctatctggtttccaatcgggagtctggagtccccagcaggttcag
cggcagtgggtctggaactgactttaccctgacaatctcctcactccagcccgaagatttcg
ccacctactattgccagcagacttggagcgaccctggacatttggacagggcacaaagtg
gagatcaagcgtacggtagcggcccatctgtcttcatcttcccgccatctgatgagcagtt
gaaatctggaactgcctctgttgtgtgcctgctgaataacttctatcccagagaggccaaag
tacagtggaaggtggataacgccctccaatcgggtaactcccaggagagtgtcacagagcag
gacagcaaggacagcacctacagcctcagcagcaccctgacgctgagcaaagcagactacga

Figure 1 continued gaaacacaaagtctacgcctgcgaagtcacccatcagggcctgagctcgcccgtcacaaaga
gcttcaacaggggagagtgttag (g) DNA encoding heavy chain of antibody CA028_496 including signal sequence (SEQ ID NO:18)
atggaatggtcctgggtcttcctgttttccttctgtcacaaccggggtgcacagcgaggt
tcagctcgttgaatccggaggcggactcgtgcagcctggggctccttgcggctgagctgcg
ctgccagtggcttcactttcagcgattacaatatggcctgggtgcgccaggcccaggcaag
ggtctggagtgggtggccacaattacctatgagggcagaaacacttattaccgggattcagt
gaaagggcgatttaccatcagcagggataatgcaaagaacagtctgtacctgcagatgaact
ctctgagagctgaggacaccgctgtctactattgtgcaagccacccagtactatgagggc
tcaatctacagattgtggtttgcccattggggccagggaacactggtgaccgtctcgagcgc
ttctacaaagggcccatccgtcttcccctggcgcctgctccaggagcacctccgagagca
cagccgccctgggctgcctggtcaaggactacttccccgaaccggtgacggtgtcgtggaac
tcaggcgccctgaccagcggcgtgcacaccttccggctgtcctacagtcctcaggactcta
ctccctcagcagcgtggtgaccgtgcctccagcagcttgggcacgaagacctacacctgca
acgtagatcacaagcccagcaacaccaaggtggacaagagagttggtgagaggccagcacag
ggagggagggtgtctgctggaagccaggctcagcctcctgcctggacgcacccggctgtg
cagccccagcccagggcagcaaggcatgccccatctgtctcctcacccggaggcctctgacc
acccactcatgcccagggagagggtcttctggatttttccaccaggctccgggcagccaca
ggctggatgcccctaccccaggccctgcgcatacaggggcaggtgctgcgctcagacctgcc
aagagccatatccgggaggaccctgcccctgacctaagccacccaaaggccaaactctcc
actccctcagctcagacaccttctctcctcccagatctgagtaactccaatcttctctctg
cagagtccaaatatggtcccccatgccaccatgcccaggtaagccaacccaggcctcgccc
tccagctcaaggcgggacaggtgccctagagtagcctgcatccagggacaggccccagccgg
gtgctgacgcatccacctccatctcttcctcagcacctgagttcctgggggggaccatcagtc
ttcctgttccccccaaaacccaaggacactctcatgatctcccggacccctgaggtcacgtg
cgtggtggtggacgtgagccaggaagaccccgaggtccagttcaactggtacgtggatggcg
tggaggtgcataatgccaagacaaagccgcgggaggagcagttcaacagcacgtaccgtgtg
gtcagcgtcctcaccgtcctgcaccaggactggctgaacggcaaggagtacaagtgcaaggt
ctccaacaaaggcctcccgtcctccatcgagaaaaccatctccaaagccaaaggtgggaccc
acggggtgcgagggccacatggacagaggtcagctcggccacccctctgcctgggagtgac
cgctgtgccaacctctgtccctacagggcagccccgagagccacaggtgtacaccctgcccc
catcccaggaggagatgaccaagaaccaggtcagcctgacctgcctggtcaaaggcttctac
cccagcgacatcgccgtggagtgggagagcaatgggcagccggagaacaactacaagaccac
gcctcccgtgctggactccgacggctccttcttcctctacagcaggctaaccgtggacaaga
gcaggtggcaggaggggaatgtcttctcatgctccgtgatgcatgaggctctgcacaaccac
tacacacagaagagcctctccctgtctctgggtaaa

SEQUENCE LISTING

<160> NUMBER OF SEQ ID NOS: 20

<210> SEQ ID NO 1
<211> LENGTH: 10
<212> TYPE: PRT
<213> ORGANISM: Rattus rattus

<400> SEQUENCE: 1

Gly Phe Thr Phe Ser Asp Tyr Asn Met Ala
1               5                   10

<210> SEQ ID NO 2
<211> LENGTH: 17
<212> TYPE: PRT
<213> ORGANISM: Artificial Sequence
<220> FEATURE:
<223> OTHER INFORMATION: CDRH2

<400> SEQUENCE: 2

Thr Ile Thr Tyr Glu Gly Arg Asn Thr Tyr Tyr Arg Asp Ser Val Lys
1               5                   10                  15

Gly

<210> SEQ ID NO 3
<211> LENGTH: 16
<212> TYPE: PRT
<213> ORGANISM: Artificial Sequence
<220> FEATURE:
<223> OTHER INFORMATION: CDRH3

-continued

<400> SEQUENCE: 3

Pro Pro Gln Tyr Tyr Glu Gly Ser Ile Tyr Arg Leu Trp Phe Ala His
1               5                   10                  15

<210> SEQ ID NO 4
<211> LENGTH: 11
<212> TYPE: PRT
<213> ORGANISM: Artificial Sequence
<220> FEATURE:
<223> OTHER INFORMATION: CDRL1

<400> SEQUENCE: 4

Arg Ala Asp Glu Ser Val Thr Thr Leu Met His
1               5                   10

<210> SEQ ID NO 5
<211> LENGTH: 7
<212> TYPE: PRT
<213> ORGANISM: Rattus rattus

<400> SEQUENCE: 5

Leu Val Ser Asn Arg Glu Ser
1               5

<210> SEQ ID NO 6
<211> LENGTH: 9
<212> TYPE: PRT
<213> ORGANISM: Rattus rattus

<400> SEQUENCE: 6

Gln Gln Thr Trp Ser Asp Pro Trp Thr
1               5

<210> SEQ ID NO 7
<211> LENGTH: 108
<212> TYPE: PRT
<213> ORGANISM: Artificial Sequence
<220> FEATURE:
<223> OTHER INFORMATION: gL7

<400> SEQUENCE: 7

Ala Ile Gln Leu Thr Gln Ser Pro Ser Ser Leu Ser Ala Ser Val Gly
1               5                   10                  15

Asp Arg Val Thr Ile Thr Cys Arg Ala Asp Glu Ser Val Thr Thr Leu
            20                  25                  30

Met His Trp Tyr Gln Lys Pro Gly Lys Ala Pro Lys Leu Leu Ile
        35                  40                  45

Tyr Leu Val Ser Asn Arg Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Trp Ser Asp Pro Trp
                85                  90                  95

Thr Phe Gly Gln Gly Thr Lys Val Glu Ile Lys Arg
            100                 105

<210> SEQ ID NO 8
<211> LENGTH: 324
<212> TYPE: DNA
<213> ORGANISM: Artificial Sequence
<220> FEATURE:
<223> OTHER INFORMATION: gL7

<400> SEQUENCE: 8

```
gccatccagc tgacccagag cccttcctct ctcagcgcca gtgtcggaga cagagtgact     60
attacctgca gggctgacga aagcgtgacc acattgatgc actggtacca acagaagcct    120
ggcaaagccc ccaagctcct gatctatctg gtttccaatc gggagtctgg agtccccagc    180
aggttcagcg gcagtgggtc tggaactgac tttaccctga caatctcctc actccagccc    240
gaagatttcg ccacctacta ttgccagcag acttggagcg accttggac atttggacag     300 ggcacaaaag tggagatcaa gcgt                                           324
```

<210> SEQ ID NO 9
<211> LENGTH: 125
<212> TYPE: PRT
<213> ORGANISM: Artificial Sequence
<220> FEATURE:
<223> OTHER INFORMATION: gH9

<400> SEQUENCE: 9

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Asn Met Ala Trp Val Arg Gln Ala Pro Gly Lys Gly Leu Glu Trp Val
        35                  40                  45

Ala Thr Ile Thr Tyr Glu Gly Arg Asn Thr Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Pro Pro Gln Tyr Tyr Glu Gly Ser Ile Tyr Arg Leu Trp Phe
           100                 105                 110

Ala His Trp Gly Gln Gly Thr Leu Val Thr Val Ser Ser
           115                 120                 125
```

<210> SEQ ID NO 10
<211> LENGTH: 375
<212> TYPE: DNA
<213> ORGANISM: Artificial Sequence
<220> FEATURE:
<223> OTHER INFORMATION: gH9

<400> SEQUENCE: 10

```
gaggttcagc tcgttgaatc cggaggcgga ctcgtgcagc ctgggggctc cttgcggctg     60
agctgcgctg ccagtggctt cacttttcagc gattacaata tggcctgggt gcgccaggcc   120
ccaggcaagg gtctggagtg gtggccaca attacctatg agggcagaaa cacttattac     180
cgggattcag tgaaagggcg atttaccatc agcaggata atgcaaagaa cagtctgtac    240
ctgcagatga actctctgag agctgaggac accgctgtct actattgtgc aagcccaccc   300
cagtactatg agggctcaat ctacagattg tggtttgccc attggggcca gggaacactg   360
gtgaccgtct cgagc                                                    375
```

<210> SEQ ID NO 11
<211> LENGTH: 214
<212> TYPE: PRT
<213> ORGANISM: Artificial Sequence
<220> FEATURE:
<223> OTHER INFORMATION: GL7+constant domain

<400> SEQUENCE: 11

```
Ala Ile Gln Leu Thr Gln Ser Pro Ser Ser Leu Ser Ala Ser Val Gly
1               5                   10                  15

Asp Arg Val Thr Ile Thr Cys Arg Ala Asp Glu Ser Val Thr Thr Leu
            20                  25                  30

Met His Trp Tyr Gln Gln Lys Pro Gly Lys Ala Pro Lys Leu Leu Ile
        35                  40                  45

Tyr Leu Val Ser Asn Arg Glu Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Thr Trp Ser Asp Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 234
<212> TYPE: PRT
<213> ORGANISM: Artificial Sequence
<220> FEATURE:
<223> OTHER INFORMATION: Signal+gL7+constant domain

<400> SEQUENCE: 12

Met Ser Val Pro Thr Gln Val Leu Gly Leu Leu Leu Leu Trp Leu Thr
1               5                   10                  15

Asp Ala Arg Cys Ala Ile Gln Leu Thr Gln Ser Pro Ser Ser Leu Ser
            20                  25                  30

Ala Ser Val Gly Asp Arg Val Thr Ile Thr Cys Arg Ala Asp Glu Ser
        35                  40                  45

Val Thr Thr Leu Met His Trp Tyr Gln Gln Lys Pro Gly Lys Ala Pro
    50                  55                  60

Lys Leu Leu Ile Tyr Leu Val Ser Asn Arg Glu Ser Gly Val Pro Ser
65              70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Thr Trp
            100                 105                 110

Ser Asp Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140
```

```
Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 13
<211> LENGTH: 645
<212> TYPE: DNA
<213> ORGANISM: Artificial Sequence
<220> FEATURE:
<223> OTHER INFORMATION: gL7+constant domain

<400> SEQUENCE: 13

```
gccatccagc tgacccagag cccttcctct ctcagcgcca gtgtcggaga cagagtgact       60
attacctgca gggctgacga aagcgtgacc acattgatgc actggtacca acagaagcct      120
ggcaaagccc ccaagctcct gatctatctg gtttccaatc gggagtctgg agtccccagc      180
aggttcagcg gcagtgggtc tggaactgac tttaccctga caatctcctc actccagccc      240
gaagatttcg ccacctacta ttgccagcag acttggagcg accttggaca tttggacag      300
ggcacaaaag tggagatcaa gcgtacggta gcggccccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga aaacacaaa gtctacgcct gcgaagtcac ccatcagggc      600
ctgagctcgc ccgtcacaaa gagcttcaac aggggagagt gttag                    645
```

<210> SEQ ID NO 14
<211> LENGTH: 705
<212> TYPE: DNA
<213> ORGANISM: Artificial Sequence
<220> FEATURE:
<223> OTHER INFORMATION: signal+gL7+constant domain

<400> SEQUENCE: 14

```
atgtcagttc ccacacaggt gctgggcctg cttctgttgt ggctcaccga tgctaggtgt       60
gccatccagc tgacccagag cccttcctct ctcagcgcca gtgtcggaga cagagtgact      120
attacctgca gggctgacga aagcgtgacc acattgatgc actggtacca acagaagcct      180
ggcaaagccc ccaagctcct gatctatctg gtttccaatc gggagtctgg agtccccagc      240
aggttcagcg gcagtgggtc tggaactgac tttaccctga caatctcctc actccagccc      300
gaagatttcg ccacctacta ttgccagcag acttggagcg accttggaca tttggacag      360
ggcacaaaag tggagatcaa gcgtacggta gcggccccat ctgtcttcat cttcccgcca      420
tctgatgagc agttgaaatc tggaactgcc tctgttgtgt gcctgctgaa taacttctat      480
cccagagagg ccaaagtaca gtggaaggtg gataacgccc tccaatcggg taactcccag      540
gagagtgtca cagagcagga cagcaaggac agcacctaca gcctcagcag caccctgacg      600
```

-continued

```
ctgagcaaag cagactacga gaaacacaaa gtctacgcct gcgaagtcac ccatcagggc    660
ctgagctcgc ccgtcacaaa gagcttcaac aggggagagt gttag                   705
```

<210> SEQ ID NO 15
<211> LENGTH: 452
<212> TYPE: PRT
<213> ORGANISM: Artificial Sequence
<220> FEATURE:
<223> OTHER INFORMATION: gH9+constant domain

<400> SEQUENCE: 15

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asn Met Ala Trp Val Arg Gln Ala Pro Gly Lys Gly Leu Glu Trp Val
        35                  40                  45

Ala Thr Ile Thr Tyr Glu Gly Arg Asn Thr Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Pro Pro Gln Tyr Tyr Glu Gly Ser Ile Tyr Arg Leu Trp Phe
            100                 105                 110

Ala His Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350
```

```
Val Tyr Thr Leu Pro Pro Ser Gln Glu Glu Met Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
                420                 425                 430

Met His Glu Ala Leu His Asn His Tyr Thr Gln Lys Ser Leu Ser Leu
                435                 440                 445

Ser Leu Gly Lys
        450

<210> SEQ ID NO 16
<211> LENGTH: 471
<212> TYPE: PRT
<213> ORGANISM: Artificial Sequence
<220> FEATURE:
<223> OTHER INFORMATION: signal+gH9+constant domain

<400> SEQUENCE: 16

Met Glu Trp Ser Trp Val Phe Leu Phe Phe Leu Ser Val Thr Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asp Tyr Asn Met Ala Trp Val Arg Gln Ala Pro Gly Lys Gly Leu
    50                  55                  60

Glu Trp Val Ala Thr Ile Thr Tyr Glu Gly Arg Asn Thr Tyr Tyr Arg
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Ser Pro Pro Gln Tyr Glu Gly Ser Ile Tyr Arg
        115                 120                 125

Leu Trp Phe Ala His Trp Gly Gln Gly Thr Leu Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Lys Thr
    210                 215                 220

Tyr Thr Cys Asn Val Asp His Lys Pro Ser Asn Thr Lys Val Asp Lys
225                 230                 235                 240

Arg Val Glu Ser Lys Tyr Gly Pro Pro Cys Pro Pro Cys Pro Ala Pro
                245                 250                 255

Glu Phe Leu Gly Gly Pro Ser Val Phe Leu Phe Pro Pro Lys Pro Lys
```

```
                  260              265              270
Asp Thr Leu Met Ile Ser Arg Thr Pro Glu Val Thr Cys Val Val Val
            275                 280                 285

Asp Val Ser Gln Glu Asp Pro Glu Val Gln Phe Asn Trp Tyr Val Asp
        290                 295                 300

Gly Val Glu Val His Asn Ala Lys Thr Lys Pro Arg Glu Glu Gln Phe
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Gly Leu
            340                 345                 350

Pro Ser Ser Ile Glu Lys Thr Ile Ser Lys Ala Lys Gly Gln Pro Arg
        355                 360                 365

Glu Pro Gln Val Tyr Thr Leu Pro Pro Ser Gln Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Arg Leu Thr Val Asp Lys Ser Arg Trp Gln Glu Gly Asn Val Phe Ser
        435                 440                 445

Cys Ser Val Met His Glu Ala Leu His Asn His Tyr Thr Gln Lys Ser
    450                 455                 460

Leu Ser Leu Ser Leu Gly Lys
465                 470

<210> SEQ ID NO 17
<211> LENGTH: 1963
<212> TYPE: DNA
<213> ORGANISM: Artificial Sequence
<220> FEATURE:
<223> OTHER INFORMATION: gH9+constant domain

<400> SEQUENCE: 17
gaggttcagc tcgttgaatc cggaggcgga ctcgtgcagc tgggggctc cttgcggctg      60 agctgcgctg ccagtggctt cactttcagc gattacaata tggcctgggt gcgccaggcc     120
ccaggcaagg gtctggagtg gtggccaca attacctatg agggcagaaa cacttattac     180
cgggattcag tgaaagggcg atttaccatc agcagggata tgcaaagaa cagtctgtac     240 ctgcagatga actctctgag agctgaggac accgctgtct actattgtgc aagcccaccc     300
cagtactatg agggctcaat ctacagattg tggtttgccc attggggcca gggaacactg     360
gtgaccgtct cgagcgcttc tacaaagggc ccatccgtct tccccctggc gccctgctcc     420
aggagcacct ccgagagcac agccgccctg ggctgcctgg tcaaggacta cttccccgaa     480
ccggtgacgg tgtcgtggaa ctcaggcgcc ctgaccagcg gcgtgcacac cttcccggct     540
gtcctacagt cctcaggact ctactccctc agcagcgtgg tgaccgtgcc ctccagcagc     600
ttgggcacga agacctacac ctgcaacgta gatcacaagc ccagcaacac caaggtggac     660
aagagagttg gtgagaggcc agcacaggga gggagggtgt ctgctggaag ccaggctcag     720
ccctcctgcc tggacgcacc ccggctgtgc agcccagcc agggcagca aggcatgccc     780 catctgtctc ctcacccgga ggcctctgac caccccactc atgcccaggg agagggtctt     840
ctggattttt tccaccaggct ccgggcagcc acaggctgga tgcccctacc ccaggccctg     900
```

```
cgcatacagg ggcaggtgct gcgctcagac ctgccaagag ccatatccgg gaggaccctg      960
cccctgacct aagcccaccc caaaggccaa actctccact ccctcagctc agacaccttc     1020
tctcctccca gatctgagta actcccaatc ttctctctgc agagtccaaa tatggtcccc     1080
catgcccacc atgcccaggt aagccaaccc aggcctcgcc ctccagctca aggcgggaca     1140
ggtgccctag agtagcctgc atccaggac aggcccagc cgggtgctga cgcatccacc       1200
tccatctctt cctcagcacc tgagttcctg gggggaccat cagtcttcct gttcccccca    1260
aaacccaagg acactctcat gatctcccgg acccctgagg tcacgtgcgt ggtggtggac     1320
gtgagccagg aagaccccga ggtccagttc aactggtacg tggatggcgt ggaggtgcat    1380
aatgccaaga caaagccgcg ggaggagcag ttcaacagca cgtaccgtgt ggtcagcgtc    1440
ctcaccgtcc tgcaccagga ctggctgaac ggcaaggagt acaagtgcaa ggtctccaac    1500
aaaggcctcc cgtcctccat cgagaaaacc atctccaaag ccaaaggtgg acccacgggg    1560
gtgcgagggc cacatggaca gaggtcagct cggcccaccc tctgccctgg gagtgaccgc    1620
tgtgccaacc tctgtcccta cagggcagcc ccgagagcca caggtgtaca ccctgccccc    1680
atcccaggag gagatgacca agaaccaggt cagcctgacc tgcctggtca aaggcttcta    1740
ccccagcgac atcgccgtgg agtgggagag caatgggcag ccggagaaca actacaagac    1800
cacgcctccc gtgctggact ccgacggctc cttcttcctc tacagcaggc taaccgtgga    1860
caagagcagg tggcaggagg ggaatgtctt ctcatgctcc gtgatgcatg aggctctgca    1920
caaccactac acacagaaga gcctctccct gtctctgggt aaa                      1963

<210> SEQ ID NO 18
<211> LENGTH: 2020
<212> TYPE: DNA
<213> ORGANISM: Artificial Sequence
<220> FEATURE:
<223> OTHER INFORMATION: signal+gH9+constant domain

<400> SEQUENCE: 18
atggaatggt cctgggtctt cctgtttttc ctttctgtca caaccggggt gcacagcgag       60
gttcagctcg ttgaatccgg aggcggactc gtgcagcctg ggggctcctt gcggctgagc      120
tgcgctgcca gtggcttcac tttcagcgat acaatatgg cctgggtgcg ccaggccca       180 ggcaagggtc tggagtgggt ggccacaatt acctatgagg cagaaacac ttattaccgg       240 gattcagtga aggggcgatt taccatcagc agggataatg caagaacag tctgtacctg       300 cagatgaact ctctgagagc tgaggacacc gctgtctact attgtgcaag cccaccccag      360
tactatgagg gctcaatcta cagattgtgg tttgcccatt ggggccaggg aacactggtg      420
accgtctcga gcgcttctac aaagggccca tccgtcttcc ccctggcgcc ctgctccagg      480
agcacctccg agagcacagc cgccctgggc tgcctggtca aggactactt ccccgaaccg     540
gtgacggtgt cgtggaactc aggcgccctg accagcggcg tgcacacctt cccggctgtc     600
ctacagtcct caggactcta ctccctcagc agcgtggtga ccgtgccctc agcagcttg      660 ggcacgaaga cctacacctg caacgtagat cacaagccca gcaacaccaa ggtggacaag     720
agagttggtg agaggccagc acagggaggg agggtgtctg ctggaagcca ggctcagccc    780
tcctgcctgg acgcaccccg gctgtgcagc cccagcccag gcagcaagg catgcccat      840 ctgtctcctc acccggaggc ctctgaccac cccactcatg cccagggaga gggtcttctg     900
gatttttcca ccaggctccg ggcagccaca ggctggatgc cctacccca ggccctgcgc     960 atacaggggc aggtgctgcg ctcagacctg ccaagagcca tatccgggag gaccctgccc    1020
```

-continued

```
ctgacctaag cccaccccaa aggccaaact ctccactccc tcagctcaga caccttctct    1080
cctcccagat ctgagtaact cccaatcttc tctctgcaga gtccaaatat ggtccccat    1140 gcccaccatg cccaggtaag ccaacccagg cctcgccctc cagctcaagg cgggacaggt    1200
gccctagagt agcctgcatc cagggacagg ccccagccgg gtgctgacgc atccacctcc    1260
atctcttcct cagcacctga gttcctgggg ggaccatcag tcttcctgtt cccccccaaa    1320
cccaaggaca ctctcatgat ctcccggacc cctgaggtca cgtgcgtggt ggtggacgtg    1380
agccaggaag accccgaggt ccagttcaac tggtacgtgg atggcgtgga ggtgcataat    1440
gccaagacaa agccgcggga ggagcagttc aacagcacgt accgtgtggt cagcgtcctc    1500
accgtcctgc accaggactg gctgaacggc aaggagtaca agtgcaaggt ctccaacaaa    1560
ggcctcccgt cctccatcga aaaaccatc tccaaagcca aaggtgggac ccacggggtg    1620
cgagggccac atggacagag gtcagctcgg cccaccctct gcctgggag tgaccgctgt    1680 gccaacctct gtcctacag gcagccccg agagccacg tgtacaccc tgcccccatc    1740 ccaggaggag atgaccaaga accaggtcag cctgacctgc ctggtcaaag cttctaccc    1800 cagcgacatc gccgtggagt gggagagcaa tgggcagccg gagaacaact acaagaccac    1860
gcctcccgtg ctggactccg acggctcctt cttcctctac agcaggctaa ccgtggacaa    1920
gagcaggtgg caggagggga atgtcttctc atgctccgtg atgcatgagg ctctgcacaa    1980
ccactacaca cagaagagcc tctccctgtc tctgggtaaa    2020
```

<210> SEQ ID NO 19
<211> LENGTH: 286
<212> TYPE: PRT
<213> ORGANISM: Artificial Sequence
<220> FEATURE:
<223> OTHER INFORMATION: IL-17A/F heterodimer

<400> SEQUENCE: 19

```
Met Gly Ile Thr Ile Pro Arg Asn Pro Gly Cys Pro Asn Ser Glu Asp
1               5                   10                  15

Lys Asn Phe Pro Arg Thr Val Met Val Asn Leu Asn Ile His Asn Arg
            20                  25                  30

Asn Thr Asn Thr Asn Pro Lys Arg Ser Ser Asp Tyr Tyr Asn Arg Ser
        35                  40                  45

Thr Ser Pro Trp Asn Leu His Arg Asn Glu Asp Pro Glu Arg Tyr Pro
    50                  55                  60

Ser Val Ile Trp Glu Ala Lys Cys Arg His Leu Gly Cys Ile Asn Ala
65                  70                  75                  80

Asp Gly Asn Val Asp Tyr His Met Asn Ser Val Pro Ile Gln Gln Glu
                85                  90                  95

Ile Leu Val Leu Arg Arg Glu Pro Pro His Cys Pro Asn Ser Phe Arg
            100                 105                 110

Leu Glu Lys Ile Leu Val Ser Val Gly Cys Thr Cys Val Thr Pro Ile
        115                 120                 125

Val His His Val Ala Gly Gly Gly Ser Gly Gly Gly Gly Ser Gly
    130                 135                 140

Gly Gly Ser Gly Gly Gly Ser Arg Lys Ile Pro Lys Val Gly
145                 150                 155                 160

His Thr Phe Phe Gln Lys Pro Glu Ser Cys Pro Pro Val Pro Gly Gly
                165                 170                 175

Ser Met Lys Leu Asp Ile Gly Ile Ile Asn Glu Asn Gln Arg Val Ser
            180                 185                 190
```

```
Met Ser Arg Asn Ile Glu Ser Arg Ser Thr Ser Pro Trp Asn Tyr Thr
            195                 200                 205

Val Thr Trp Asp Pro Asn Arg Tyr Pro Ser Glu Val Val Gln Ala Gln
        210                 215                 220

Cys Arg Asn Leu Gly Cys Ile Asn Ala Gln Gly Lys Glu Asp Ile Ser
225                 230                 235                 240

Met Asn Ser Val Pro Ile Gln Gln Glu Thr Leu Val Val Arg Arg Lys
                245                 250                 255

His Gln Gly Cys Ser Val Ser Phe Gln Leu Glu Lys Val Leu Val Thr
            260                 265                 270

Val Gly Cys Thr Cys Val Thr Pro Val Ile His His Val Gln
        275                 280                 285

<210> SEQ ID NO 20
<211> LENGTH: 134
<212> TYPE: PRT
<213> ORGANISM: Artificial Sequence
<220> FEATURE:
<223> OTHER INFORMATION: Cynomolgus IL-17F

<400> SEQUENCE: 20

Met Arg Lys Ile Pro Lys Val Gly His Thr Phe Phe Gln Lys Pro Glu
1               5                   10                  15

Ser Cys Pro Pro Val Pro Glu Gly Ser Met Lys Leu Asp Thr Gly Ile
                20                  25                  30

Ile Asn Glu Asn Gln Arg Val Ser Met Ser Arg Asn Ile Glu Ser Arg
            35                  40                  45

Ser Thr Ser Pro Trp Asn Tyr Thr Val Thr Trp Asp Pro Asn Arg Tyr
        50                  55                  60

Pro Ser Glu Val Val Gln Ala Gln Cys Lys His Leu Gly Cys Ile Asn
65                  70                  75                  80

Ala Gln Gly Lys Glu Asp Ile Ser Met Asn Ser Val Pro Ile Gln Gln
                85                  90                  95

Glu Thr Leu Val Leu Arg Arg Lys His Gln Gly Cys Ser Val Ser Phe
            100                 105                 110

Gln Leu Glu Lys Val Leu Val Thr Val Gly Cys Thr Cys Val Thr Pro
        115                 120                 125

Val Ile His His Val Gln
        130
```

NUCLEIC ACIDS ENCODING ANTIBODY MOLECULES WHICH BIND IL-17A AND IL-17F

This application is divisional of U.S. application Ser. No. 12/446,143, filed Jun. 11, 2010, which is a national phase entry of International Application No. PCT/GB2007/003983, filed Oct. 18, 2007, now U.S. Pat. No. 8,303,953, which claims the benefit of Great Britain Application No. 0620729.4, filed Oct. 18, 2006, the disclosures of which are incorporated by reference herein.

The present invention relates to antibody molecules having specificity for antigenic determinants of both IL-17A and IL-17F. The present invention also relates to the therapeutic uses of the antibody molecules and methods for producing them.

Interleukin 17 (IL-17), also known as CTLA-8 or IL-17A, is a pro-inflammatory cytokine which stimulates the secretion of a wide range of other cytokines from various non-immune cells. IL-17A is capable of inducing the secretion of IL-6, IL-8, PGE2, MCP-1 and G-CSF by adherent cells like fibroblasts, keratinocytes, epithelial and endothelial cells and is also able to induce ICAM-1 surface expression, proliferation of T cells, and growth and differentiation of CD34+ human progenitors into neutrophils when cocultured in the presence of irradiated fibroblasts (Fossiez et al., 1998, Int. Rev. Immunol. 16, 541-551). IL-17A is predominantly produced by activated memory T cells and acts by binding to a ubiquitously distributed cell surface receptor (IL-17R) (Yao et al., 1997, Cytokine, 9, 794-800). It may also act through binding to a complex of IL-17RA and IL-17RC (Toy et al., 2006, J. Immunol. 177(11); 36-39). IL-17 producing T cells called 'TH17 cells' have been implicated in the pathogenesis of certain cancers (Weaver et al., 2006, Immunity, 24, 677-688; Langowski et al., 2006, 442, 461-465; Iwakura and Ishigame, 2006, J. Clin. Invest. 116, 5, 1218-1222).

A number of homologues of IL-17 have been identified which have both similar and distinct roles in regulating inflammatory responses. For a review of IL-17 cytokine/receptor families see Dumont, 2003, Expert Opin. Ther. Patents, 13, 287-303. One such homologue is IL-17F, also known as IL-24 and ML-1, which is around 55% identical to IL-17A and is thought to share the same receptors as IL-17A (Kolls and Linden 2004, Immunity, 21, 467-476; Hymowitz, et al., 2001, EMBO J. 20(19), 5332-5341; Kuestner et al., 2007, Journal of Immunology, 179, 5462-5473).

Both IL-17A and IL-17F can form both homodimeric and heterodimeric proteins, all of which are produced by activated human CD4+ T cells (Wright et al., 2007, J Biol. Chem. 282 (18), 13447-13455).

IL-17 may contribute to a number of diseases mediated by abnormal immune responses, such as rheumatoid arthritis and air-way inflammation, as well as organ transplant rejection and antitumour immunity. Inhibitors of IL-17 activity are well known in the art for example a murine IL-17R:human Fc fusion protein, a murine soluble IL-17R and an anti-IL-17 monoclonal antibody have been used to demonstrate the role of IL-17 in various models of rheumatoid arthritis (Lubberts et al., J. Immunol. 2001, 167, 1004-1013; Chabaud et al., Arthritis Res. 2001, 3, 168-177). In addition, neutralising polyclonal antibodies have been used to reduce peritoneal adhesion formation (Chung et al., 2002, J. Exp. Med., 195, 1471-1478). Rat derived anti-human IL-17 antibodies were described in WO04/106377. A humanised anti-IL-17 antibody with an affinity of around 220 pM was described in WO2006/054059. A monoclonal anti-IL-17 fully human antibody with an affinity of around 188 pM was described in WO2006/013107. Antibodies which bind IL-17F and IL-17A/IL-17F heterodimers were described in WO2006/088833. Antibodies which specifically bind the IL-17A/IL-17F heterodimer were described in WO2005/010044.

IL-17F antagonism has been associated with protection against asthma (Kawaguchi et al., 2006, J. Allergy Clin. Immunol. 117(4); 795-801) and IL-17F is also thought to play a role in arthritis pathology (Lubberts 2003, Current Opinion in Investigational Drugs, 4 (5), 572-577).

Accordingly dual antagonists of IL-17A and IL-17F may be more effective than a sole antagonist in treating IL-17 mediated diseases. Antibodies which bind IL-17A and IL-17F were described in WO2007/106769 published 20.9.07.

We have been able to demonstrate that it is possible to isolate an antibody which is capable of binding to both IL-17A and IL-17F and is capable of neutralising the activity of both isoforms of IL-17. Hence the present invention provides an anti-IL-17 antibody which is capable of binding to both IL-17A and IL-17F. In particular, the antibody of the present invention is capable of specifically binding to both IL-17A and IL-17F i.e. the antibody does not bind to other isoforms of IL-17. Preferably the antibody of the present invention also binds the IL-17A/IL-17F heterodimer. Preferably, the antibody of the present invention neutralises the activity of both IL-17A and IL-17F. In one embodiment the antibody of the present invention also neutralises the activity of the IL-17A/IL-17F heterodimer. The antibodies of the present invention therefore have the advantageous property that they can inhibit the biological activity of both IL-17A and IL-17F. Accordingly, the present invention also provides the use of such antibodies in the treatment of and/or prophylaxis of a disease mediated by either or both of IL-17A or IL-17F such as autoimmune or inflammatory disease or cancer.

As used herein, the term 'neutralising antibody' describes an antibody that is capable of neutralising the biological signalling activity of both IL-17A and IL17F for example by blocking binding of IL-17A and IL17F to one or more of their receptors and by blocking binding of the IL-17A/IL-17F heterodimer to one or more of its receptors. It will be appreciated that the term 'neutralising' as used herein refers to a reduction in biological signalling activity which may be partial or complete. Further, it will be appreciated that the extent of neutralisation of IL-17A and IL-17F activity by the antibody may be the same or different. In one embodiment the extent of neutralisation of the activity of the IL-17A/IL-17F heterodimer may be the same or different as the extent of neutralisation of IL-17A or IL-17F activity.

In one embodiment the antibodies of the present invention specifically bind to IL-17A and IL-17F. Specifically binding means that the antibodies have a greater affinity for IL-17A and IL-17F polypeptides (including the IL-17A/IL-17F heterodimer) than for other polypeptides. Preferably the IL-17A and IL-17F polypeptides are human. In one embodiment the antibody also binds cynomolgus IL-17F.

IL-17A or IL-17F polypeptides or a mixture of the two or cells expressing one or both of said polypeptides can be used to produce antibodies which specifically recognise both polypeptides. The IL-17 polypeptides (IL-17A and IL-17F) may be 'mature' polypeptides or biologically active fragments or derivatives thereof which preferably include the receptor binding site. Preferably the IL-17 polypeptides are the mature polypeptides. IL-17 polypeptides may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. The IL-17 polypeptide may in some instances be part of a larger protein such as a fusion protein for example fused to an affinity tag. Antibodies generated against these polypeptides may be obtained, where immunisation of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows or pigs may be immunized. However, mice, rabbits, pigs and rats are generally preferred.

Antibodies for use in the present invention include whole antibodies and functionally active fragments or derivatives thereof and may be, but are not limited to, monoclonal, multivalent, multi-specific, humanized or chimeric antibodies, domain antibodies e.g. VH, VL, VHH, single chain antibodies, Fab fragments, Fab' and F(ab')$_2$ fragments and epitope-binding fragments of any of the above. Other antibody fragments include those described in International patent applications WO2005003169, WO2005003170 and WO2005003171. Antibody fragments and methods of producing them are well known in the art, see for example Verma et al., 1998, Journal of Immunological Methods, 216, 165-181; Adair and Lawson, 2005. Therapeutic antibodies. *Drug Design Reviews—Online* 2(3):209-217.

Antibodies for use in the present invention include immunoglobulin molecules and immunologically active portions of immunoglobulin molecules, i.e. molecules that contain an antigen binding site that specifically binds an antigen. The immunoglobulin molecules of the invention can be of any class (e.g. IgG, IgE, IgM, IgD and IgA) or subclass of immunoglobulin molecule.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by for example the methods described by Babcook, J. et al., 1996, Proc. Natl. Acad. Sci. USA 93(15): 7843-78481; WO92/02551; WO2004/051268 and International Patent Application number WO2004/106377.

Humanized antibodies are antibody molecules from non-human species having one or more complementarity determining regions (CDRs) from the non-human species and a framework region from a human immunoglobulin molecule (see, e.g. U.S. Pat. No. 5,585,089; WO91/09967).

Chimeric antibodies are those antibodies encoded by immunoglobulin genes that have been genetically engineered so that the light and heavy chain genes are composed of immunoglobulin gene segments belonging to different species. These chimeric antibodies are likely to be less antigenic. Bivalent antibodies may be made by methods known in the art (Milstein et al., 1983, Nature 305:537-539; WO 93/08829, Traunecker et al., 1991, EMBO J. 10:3655-3659). Multivalent antibodies may comprise multiple specificities or may be monospecific (see for example WO 92/22853 and WO05/113605).

The antibodies for use in the present invention can also be generated using various phage display methods known in the art and include those disclosed by Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280) and WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108. Techniques for the production of single chain antibodies, such as those described in U.S. Pat. No. 4,946,778 can also be adapted to produce single chain antibodies which bind to IL-17A and IL-17F. Also, transgenic mice, or other organisms, including other mammals, may be used to express humanized antibodies.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus 'CDR-H1', as used herein, comprises residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

In one embodiment the present invention provides a neutralising antibody having specificity for human IL-17A and human IL-17F, comprising a heavy chain, wherein the variable domain of the heavy chain comprises at least one of a CDR having the sequence given in SEQ ID NO:1 for CDR-H1, a CDR having the sequence given in SEQ ID NO:2 for CDR-H2 and a CDR having the sequence given in SEQ ID NO:3 for CDR-H3.

In another embodiment the present invention provides a neutralising antibody having specificity for human IL-17A and human IL-17F, comprising a heavy chain, wherein at least two of CDR-H1, CDR-H2 and CDR-H3 of the variable domain of the heavy chain are selected from the following: the sequence given in SEQ ID NO:1 for CDR-H1, the sequence given in SEQ ID NO:2 for CDR-H2 and the sequence given in SEQ ID NO:3 for CDR-H3. For example, the antibody may comprise a heavy chain wherein CDR-H1 has the sequence given in SEQ ID NO:1 and CDR-H2 has the sequence given in SEQ ID NO:2. Alternatively, the antibody may comprise a heavy chain wherein CDR-H1 has the sequence given in SEQ ID NO:1 and CDR-H3 has the sequence given in SEQ ID NO:3, or the antibody may comprise a heavy chain wherein CDR-H2 has the sequence given in SEQ ID NO:2 and CDR-H3 has the sequence given in SEQ ID NO:3. For the avoidance of doubt, it is understood that all permutations are included.

In another embodiment the present invention provides a neutralising antibody having specificity for human IL-17A and human IL-17F, comprising a heavy chain, wherein the variable domain of the heavy chain comprises the sequence given in SEQ ID NO:1 for CDR-H1, the sequence given in SEQ ID NO:2 for CDR-H2 and the sequence given in SEQ ID NO:3 for CDR-H3.

In one embodiment the present invention provides a neutralising antibody having specificity for human IL-17A and human IL-17F, comprising a light chain, wherein the variable domain of the light chain comprises at least one of a CDR having the sequence given in SEQ ID NO:4 for CDR-L1, a CDR having the sequence given in SEQ ID NO:5 for CDR-L2 and a CDR having the sequence given in SEQ ID NO:6 for CDR-L3.

In another embodiment the present invention provides a neutralising antibody having specificity for human IL-17A and human IL-17F, comprising a light chain, wherein at least two of CDR-L1, CDR-L2 and CDR-L3 of the variable domain of the light chain are selected from the following: the sequence given in SEQ ID NO:4 for CDR-L1, the sequence given in SEQ ID NO:5 for CDR-L2 and the sequence given in SEQ ID NO:6 for CDR-L3. For example, the antibody may comprise a light chain wherein CDR-L1 has the sequence given in SEQ ID NO:4 and CDR-L2 has the sequence given in SEQ ID NO:5. Alternatively, the antibody may comprise a light chain wherein CDR-L1 has the sequence given in SEQ ID NO:4 and CDR-L3 has the sequence given in SEQ ID NO:6, or the antibody may comprise a light chain wherein CDR-L2 has the sequence given in SEQ ID NO:5 and CDR-L3 has the sequence given in SEQ ID NO:6. For the avoidance of doubt, it is understood that all permutations are included.

In another embodiment the present invention provides a neutralising antibody having specificity for human IL-17A and human IL-17F, comprising a light chain, wherein the variable domain comprises the sequence given in SEQ ID NO:4 for CDR-L1, the sequence given in SEQ ID NO:5 for CDR-L2 and the sequence given in SEQ ID NO:6 for CDR-L3.

The antibody molecules of the present invention preferably comprise a complementary light chain or a complementary heavy chain, respectively.

Hence in one embodiment, an antibody according to the present invention comprises a heavy chain, wherein the variable domain of the heavy chain comprises the sequence given in SEQ ID NO:1 for CDR-H1, the sequence given in SEQ ID NO:2 for CDR-H2 and the sequence given in SEQ ID NO:3 for CDR-H3 and a light chain wherein the variable domain of the light chain comprises the sequence given in SEQ ID NO:4 for CDR-L1, the sequence given in SEQ ID NO:5 for CDR-L2 and the sequence given in SEQ ID NO:6 for CDR-L3.

It will be appreciated that one or more amino acid substitutions may be made to the CDRs provided by the present invention without significantly altering the ability of the antibody to bind to IL-17A and IL-17F and to neutralise IL-17A and IL-17F activity. The effect of any amino acid substitutions on binding and neutralisation can be readily tested by one skilled in the art, for example by using the methods described herein. Accordingly, the present invention provides an antibody comprising one or more CDRs selected from CDRH-1 (SEQ ID NO:1), CDRH-2 (SEQ ID NO:2), CDRH-3 (SEQ ID NO:3), CDRL-1 (SEQ ID NO:4), CDRL-2 (SEQ ID NO:5) and CDRL-3 (SEQ ID NO:6) in which one or more amino acids in one or more of the CDRs has been substituted with another amino acid. It will also be appreciated that the length of one or more of the CDRs may be altered without significantly altering the ability of the antibody to bind to IL-17A and IL-17F and to neutralise IL-17A and IL-17F activity.

In one embodiment, an antibody of the present invention comprises a heavy chain, wherein the variable domain of the heavy chain comprises three CDRs wherein the sequence of CDRH-1 has at least 60% identity or similarity to the sequence given in SEQ ID NO:1, CDRH-2 has at least 60% identity or similarity to the sequence given in SEQ ID NO:2 and/or CDRH-3 has at least 60% identity or similarity to the sequence given in SEQ ID NO:3. In another embodiment, an antibody of the present invention comprises a heavy chain, wherein the variable domain of the heavy chain comprises three CDRs wherein the sequence of CDRH-1 has at least 70%, 80%, 90%, 95% or 98% identity or similarity to the sequence given in SEQ ID NO:1, CDRH-2 has at least 70%, 80%, 90%, 95% or 98% identity or similarity to the sequence given in SEQ ID NO:2 and/or CDRH-3 has at least 70%, 80%, 90%, 95% or 98% identity or similarity to the sequence given in SEQ ID NO:3.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);
lysine, arginine and histidine (amino acids having basic side chains);
aspartate and glutamate (amino acids having acidic side chains);
asparagine and glutamine (amino acids having amide side chains); and
cysteine and methionine (amino acids having sulphur-containing side chains). Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

In another embodiment, an antibody of the present invention comprises a light chain, wherein the variable domain of the light chain comprises three CDRs wherein the sequence of CDRL-1 has at least 60% identity or similarity to the sequence given in SEQ ID NO:4, CDRL-2 has at least 60% identity or similarity to the sequence given in SEQ ID NO:5 and/or CDRL-3 has at least 60% identity or similarity to the sequence given in SEQ ID NO:6. In another embodiment, an antibody of the present invention comprises a light chain, wherein the variable domain of the heavy chain comprises three CDRs wherein the sequence of CDRL-1 has at least 70%, 80%, 90%, 95% or 98% identity or similarity to the sequence given in SEQ ID NO:4, CDRL-2 has at least 70%, 80%, 90%, 95% or 98% identity or similarity to the sequence given in SEQ ID NO:5 and/or CDRL-3 has at least 70%, 80%, 90%, 95% or 98% identity or similarity to the sequence given in SEQ ID NO:6.

In one embodiment the antibody provided by the present invention is a monoclonal antibody.

In one embodiment the antibody provided by the present invention is a chimeric antibody.

In one embodiment the antibody provided by the present invention is a CDR-grafted antibody molecule comprising one or more of the CDRs provided in SEQ ID NOS:1 to 6. As used herein, the term 'CDR-grafted antibody molecule' refers to an antibody molecule wherein the heavy and/or light chain contains one or more CDRs (including, if desired, one or more modified CDRs) from a donor antibody (e.g. a murine monoclonal antibody) grafted into a heavy and/or light chain variable region framework of an acceptor antibody (e.g. a human antibody). For a review, see Vaughan et al, Nature Biotechnology, 16, 535-539, 1998. In one embodiment rather than the entire CDR being transferred, only one or more of the specificity determining residues from any one of the CDRs described herein above are transferred to the human antibody framework (see for example, Kashmiri et al., 2005, Methods, 36, 25-34). In one embodiment only the specificity determining residues from one or more of the CDRs described herein above are transferred to the human antibody framework. In another embodiment only the specificity determining residues from each of the CDRs described herein above are transferred to the human antibody framework.

When the CDRs or specificity determining residues are grafted, any appropriate acceptor variable region framework sequence may be used having regard to the class/type of the donor antibody from which the CDRs are derived, including mouse, primate and human framework regions. Preferably, the CDR-grafted antibody according to the present invention has a variable domain comprising human acceptor framework regions as well as one or more of the CDRs or specificity determining residues described above. Thus, provided in one embodiment is a neutralising CDR-grafted antibody wherein the variable domain comprises human acceptor framework regions and non-human donor CDRs.

Examples of human frameworks which can be used in the present invention are KOL, NEWM, REI, EU, TUR, TEL LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at: http://vbase.mrc-cpe.cam.ac.uk/

In a CDR-grafted antibody of the present invention, the acceptor heavy and light chains do not necessarily need to be derived from the same antibody and may, if desired, comprise composite chains having framework regions derived from different chains.

The preferred framework region for the heavy chain of the CDR-grafted antibody of the present invention is derived from the human sub-group VH3 sequence 1-3 3-07 together with JH4. Accordingly, provided is a neutralising CDR-grafted antibody comprising at least one non-human donor CDR wherein the heavy chain framework region is derived from the human subgroup sequence 1-3 3-07 together with JH4. The sequence of human JH4 is as follows: (YFDY) WGQGTLVTVSS. The YFDY motif is part of CDR-H3 and is not part of framework 4 (Ravetch, J V. et al., 1981, Cell, 27, 583-591).

The preferred framework region for the light chain of the CDR-grafted antibody of the present invention is derived from the human germline sub-group VK1 sequence 2-1-(1) L4 together with JK1. Accordingly, provided is a neutralising CDR-grafted antibody comprising at least one non-human donor CDR wherein the light chain framework region is derived from the human subgroup sequence VK1 2-1-(1) L4 together with JK1. The JK1 sequence is as follows: (WT) FGQGTKVEIK. The WT motif is part of CDR-L3 and is not part of framework 4 (Hieter, P A., et al., 1982, J. Biol. Chem., 257, 1516-1522).

Also, in a CDR-grafted antibody of the present invention, the framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO 91/09967.

Preferably, in a CDR-grafted antibody molecule of the present invention, if the acceptor heavy chain has the human VH3 sequence 1-3 3-07 together with JH4, then the acceptor framework regions of the heavy chain comprise, in addition to one or more donor CDRs, a donor residue at at least position 94 (according to Kabat et al., (supra)). Accordingly, provided is a CDR-grafted antibody, wherein at least the residue at position 94 of the variable domain of the heavy chain is a donor residue.

Preferably, in a CDR-grafted antibody molecule according to the present invention, if the acceptor light chain has the human sub-group VK1 sequence 2-1-(1) L4 together with JK1, then no donor residues are transferred i.e. only the CDRs are transferred. Accordingly, provided is a CDR-grafted antibody wherein only the CDRs are transferred to the donor framework.

Donor residues are residues from the donor antibody, i.e. the antibody from which the CDRs were originally derived.

In one embodiment, an antibody of the present invention comprises a heavy chain, wherein the variable domain of the heavy chain comprises the sequence given in SEQ ID NO:9 (gH9).

In another embodiment, an antibody of the present invention comprises a heavy chain, wherein the variable domain of the heavy chain comprises a sequence having at least 60% identity or similarity to the sequence given in SEQ ID NO:9. In one embodiment, an antibody of the present invention comprises a heavy chain, wherein the variable domain of the heavy chain comprises a sequence having at least 70%, 80%, 90%, 95% or 98% identity or similarity to the sequence given in SEQ ID NO:9.

In one embodiment, an antibody of the present invention comprises a light chain, wherein the variable domain of the light chain comprises the sequence given in SEQ ID NO:7 (gL7).

In another embodiment, an antibody of the present invention comprises a light chain, wherein the variable domain of the light chain comprises a sequence having at least 60% identity or similarity to the sequence given in SEQ ID NO:7. In one embodiment the antibody of the present invention comprises a light chain, wherein the variable domain of the light chain comprises a sequence having at least 70%, 80%, 90%, 95% or 98% identity or similarity to the sequence given in SEQ ID NO:7.

In one embodiment an antibody of the present invention comprises a heavy chain, wherein the variable domain of the heavy chain comprises the sequence given in SEQ ID NO:9 and a light chain, wherein the variable domain of the light chain comprises the sequence given in SEQ ID NO:7.

In another embodiment of the invention, the antibody comprises a heavy chain and a light chain, wherein the variable domain of the heavy chain comprises a sequence having at least 60% identity or similarity to the sequence given in SEQ ID NO:9 and the variable domain of the light chain comprises a sequence having at least 60% identity or similarity to the sequence given in SEQ ID NO:7. Preferably, the antibody comprises a heavy chain, wherein the variable domain of the heavy chain comprises a sequence having at least 70%, 80%, 90%, 95% or 98% identity or similarity to the sequence given in SEQ ID NO:9 and a light chain, wherein the variable domain of the light chain comprises a sequence having at least 70%, 80%, 90%, 95% or 98% identity or similarity to the sequence given in SEQ ID NO:7.

As described herein above, the antibody molecule of the present invention may comprise a complete antibody molecule having full length heavy and light chains or a fragment thereof, such as a domain antibody e.g. VH, VL, VHH, Fab, modified Fab, Fab', F(ab')$_2$, Fv or scFv fragment.

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required, e.g. for simply blocking IL-17 activity. For example IgG4 molecules in which the serine at position 241 has been changed to proline as described in Angal et al., Molecular Immunology, 1993, 30 (1), 105-108 may be used. Particularly preferred is the IgG4 constant domain comprising this change.

In one embodiment the antibody heavy chain comprises a CH1 domain and the antibody light chain comprises a CL domain, either kappa or lambda.

In a preferred embodiment the antibody provided by the present invention is a neutralising antibody having specificity for human IL-17A and human IL-17F in which the heavy chain constant region comprises the human IgG4 constant region in which the serine at position 241 has been substituted by proline as described in Angal et al., supra. Accordingly, the present invention provides an antibody in which the heavy chain comprises or consists of the sequence given in SEQ ID NO:15.

In one embodiment of the invention, the antibody comprises a heavy chain, wherein the heavy chain comprises a sequence having at least 60% identity or similarity to the sequence given in SEQ ID NO:15. Preferably, the antibody comprises a heavy chain, wherein the heavy chain comprises a sequence having at least 70%, 80%, 90%, 95% or 98% identity or similarity to the sequence given in SEQ ID NO:15.

In one embodiment an antibody molecule according to the present invention comprises a light chain comprising the sequence given in SEQ ID NO:11.

In one embodiment of the invention, the antibody comprises a light chain, wherein the light chain comprises a sequence having at least 60% identity or similarity to the sequence given in SEQ ID NO:11. Preferably, the antibody comprises a light chain, wherein the light chain comprises a sequence having at least 70%, 80%, 90%, 95% or 98% identity or similarity to the sequence given in SEQ ID NO:11.

In one embodiment the present invention provides an antibody in which the heavy chain comprises or consists of the sequence given in SEQ ID NO:15 and the light chain comprises or consists of the sequence given in SEQ ID NO:11.

In one embodiment of the invention, the antibody comprises a heavy chain and a light chain, wherein the heavy chain comprises a sequence having at least 60% identity or similarity to the sequence given in SEQ ID NO:15 and the light chain comprises a sequence having at least 60% identity or similarity to the sequence given in SEQ ID NO:11. Preferably, the antibody comprises a heavy chain, wherein the heavy chain comprises a sequence having at least 70%, 80%, 90%, 95% or 98% identity or similarity to the sequence given in SEQ ID NO:15 and a light chain, wherein the light chain comprises a sequence having at least 70%, 80%, 90%, 95% or 98% identity or similarity to the sequence given in SEQ ID NO:11.

Also provided by the present invention is a specific region or epitope of human IL-17A and/or a specific region or epitope of human IL-17F and/or a specific region or epitope of human IL-17A/F heterodimer which is bound by an antibody provided by the present invention, in particular an antibody comprising the heavy chain sequence gH9 (SEQ ID NO:9) and/or the light chain sequence gL7 (SEQ ID NO:7).

The specific region or epitope of the human IL-17A polypeptide and the specific region or epitope of the human IL-17F polypeptide and the specific region or epitope of the human IL-17A/F heterodimer can be identified by any suitable epitope mapping method known in the art in combination with any one of the antibodies provided by the present invention. Examples of such methods include screening peptides of varying lengths derived from IL-17A and IL-17F for binding to the antibody of the present invention with the smallest fragment that can specifically bind to the antibody containing the sequence of the epitope recognised by the antibody. The IL-17 peptides may be produced synthetically or by proteolytic digestion of the appropriate IL-17 polypeptide. Peptides that bind the antibody can be identified by, for example, mass spectrometric analysis. In another example, NMR spectroscopy can be used to identify the epitope bound by an antibody of the present invention. Once identified, the epitopic fragment which binds an antibody of the present invention can be used, if required, as an immunogen to obtain additional neutralising antibodies which bind the same epitope.

Antibodies which cross-block the binding of an antibody according to the present invention, in particular, an antibody comprising the heavy chain sequence gH9 (SEQ ID NO:9) and the light chain sequence gL7 (SEQ ID NO:7), may be similarly useful in neutralising IL-17A and IL-17F activity. Accordingly, the present invention also provides a neutralising antibody which binds human IL-17A and human IL-17F, which cross-blocks the binding of any one of the antibodies described above to human IL-17A and/or human IL-17F and/or human IL-17A/F heterodimer and/or is cross-blocked from binding IL-17A and/or IL-17F and/or human IL-17A/F heterodimer by any one of those antibodies. In one embodiment, such an antibody binds to the same epitope as an antibody described herein above. In another embodiment the cross-blocking neutralising antibody binds to an epitope which borders and/or overlaps with the epitope bound by an antibody described herein above. In another embodiment the cross-blocking neutralising antibody of this aspect of the invention does not bind to the same epitope as an antibody of the present invention or an epitope that borders and/or overlaps with said epitope.

Cross-blocking antibodies can be identified using any suitable method in the art, for example by using competition ELISA or BIAcore where binding of the cross blocking antibody to human IL-17A and/or human IL-17F prevents the binding of an antibody of the present invention or vice versa.

In one embodiment there is provided a neutralising antibody which binds to human IL-17A and human IL-17F, which cross-blocks the binding of an antibody whose heavy chain comprises the sequence gH9 (SEQ ID NO:9) and whose light chain comprises the sequence gL7 (SEQ ID NO:7) to human IL-17A and to human IL-17F. In one embodiment the cross-blocking antibodies provided by the present invention inhibit the binding of an antibody comprising the heavy chain sequence gH9 (SEQ ID NO:9) and the light chain sequence gL7 (SEQ ID NO:7) to IL-17A by greater than 80%, preferably by greater than 85%, more preferably by greater than 90%, even more preferably by greater than 95% and to IL-17F by greater than 80%, preferably by greater than 85%, more preferably by greater than 90%, even more preferably by greater than 95%.

In one embodiment there is provided a neutralising antibody which binds to human IL-17A and human IL-17F, which cross-blocks the binding of an antibody whose heavy chain comprises the sequence gH9 (SEQ ID NO:9) and whose light chain comprises the sequence gL7 (SEQ ID NO:7) to human IL-17A and to human IL-17F and to human IL-17A/F heterodimer. In one embodiment the cross-blocking antibodies provided by the present invention inhibit the binding of an antibody comprising the heavy chain sequence gH9 (SEQ ID NO:9) and the light chain sequence gL7 (SEQ ID NO:7) to IL-17A by greater than 80%, preferably by greater than 85%, more preferably by greater than 90%, even more preferably by greater than 95% and to IL-17F by greater than 80%, preferably by greater than 85%, more preferably by greater than 90%, even more preferably by greater than 95% and to IL-17A/F heterodimer to IL-17F by greater than 80%, preferably by greater than 85%, more preferably by greater than 90%, even more preferably by greater than 95%.

In one embodiment there is provided a neutralising antibody which binds to human IL-17A and human IL-17F, which cross-blocks the binding of an antibody whose heavy chain comprises the sequence gH9 (SEQ ID NO:9) and whose light chain comprises the sequence gL7 (SEQ ID NO:7) to human IL-17A or to human IL-17F or human IL-17A/F heterodimer. In one embodiment the cross-blocking antibodies provided by the present invention inhibit the binding of an antibody comprising the heavy chain sequence gH9 (SEQ ID NO:9) and the light chain sequence gL7 (SEQ ID NO:7) to IL-17A or IL-17F or IL-17A/F by greater than 80%, preferably by greater than 85%, more preferably by greater than 90%, even more preferably by greater than 95%.

Alternatively or in addition, neutralising antibodies according to this aspect of the invention may be cross-blocked from binding to human IL-17A and human IL-17F by an antibody comprising the heavy chain sequence gH9 (SEQ ID NO:9) and the light chain sequence gL7 (SEQ ID NO:7). Also provided therefore is a neutralising antibody molecule which binds to human IL-17A and to human IL-17F which is cross-blocked from binding human IL-17A and human IL-17F by an antibody comprising the heavy chain sequence gH9 (SEQ ID NO:9) and the light chain sequence gL7 (SEQ ID NO:7). In one embodiment the neutralising antibodies provided by this aspect of the invention are inhibited from binding to human IL-17A and human IL-17F by an antibody comprising the heavy chain sequence gH9 (SEQ ID NO:9) and the light chain sequence gL7 (SEQ ID NO:7) by greater than 80%, preferably by greater than 85%, more preferably by greater than 90%, even more preferably by greater than 95%.

In another embodiment there is provided a neutralising antibody molecule which binds to human IL-17A and to human IL-17F which is cross-blocked from binding human IL-17A and human IL-17F and IL-17A/F heterodimer by an antibody comprising the heavy chain sequence gH9 (SEQ ID NO:9) and the light chain sequence gL7 (SEQ ID NO:7). In one embodiment the neutralising antibodies provided by this aspect of the invention are inhibited from binding to human IL-17A and human IL-17F and human IL-17A/F heterodimer by an antibody comprising the heavy chain sequence gH9 (SEQ ID NO:9) and the light chain sequence gL7 (SEQ ID NO:7) by greater than 80%, preferably by greater than 85%, more preferably by greater than 90%, even more preferably by greater than 95%.

Also provided therefore is a neutralising antibody molecule which binds to human IL-17A and to human IL-17F which is cross-blocked from binding human IL-17A or human IL-17F or human IL-17A/F by an antibody comprising the heavy chain sequence gH9 (SEQ ID NO:9) and the light chain sequence gL7 (SEQ ID NO:7). In one embodiment the neutralising antibodies provided by this aspect of the invention are inhibited from binding to human IL-17A or human IL-17F or human IL-17A/F by an antibody comprising the heavy chain sequence gH9 (SEQ ID NO:9) and the light chain sequence gL7 (SEQ ID NO:7) by greater than 80%, preferably by greater than 85%, more preferably by greater than 90%, even more preferably by greater than 95%.

The antibody molecule of any aspect of the present invention preferably has a high binding affinity, preferably nanomolar, even more preferably picomolar. It will be appreciated that the binding affinity of an antibody according to the present invention for human IL-17A may be different from the binding affinity of the same antibody for human IL-17F and/or the IL-17A/F heterodimer. In one example the antibody molecule of the present invention has an affinity for IL-17A that is greater than its affinity for IL-17F. In one example the antibody molecule of the present invention has an affinity for IL-17A which is at least 10 fold greater than its binding affinity for IL-17F. In one example the antibody molecule of the present invention has an affinity for IL-17A which is at least 50 fold greater than its binding affinity for IL-17F. In one example the antibody molecule of the present invention has an affinity for IL-17A which is at least 100 fold greater than its binding affinity for IL-17F. In one example the antibody molecule of the present invention has an affinity for IL-17F that is greater than its affinity for IL-17A. In one example the antibody molecule of the present invention has an affinity for IL-17A that is the same as its affinity for IL-17F. In one example the antibody molecule of the present invention has a picomolar affinity for IL-17A and a nanomolar affinity for IL-17F. In one example the antibody molecule of the present invention has a nanomolar affinity for IL-17F and a picomolar affinity for IL-17A. In one example the antibody molecule of the present invention has a nanomolar affinity for both IL-17A and IL-17F. In one example the antibody molecule of the present invention has a picomolar affinity for both IL-17A and IL-17F.

Preferably the antibody molecule of the present invention has a binding affinity for IL-17A of better than 10 nM. In one embodiment the antibody molecule of the present invention has a binding affinity for IL-17A of better than 500 pM. In one embodiment the antibody molecule of the present invention has a binding affinity for IL-17A of better than 100 pM. In one embodiment the antibody molecule of the present invention has a binding affinity for IL-17A of better than 20 pM. In one embodiment the antibody of the present invention has an affinity for IL-17A of 16 pM.

Preferably the antibody molecule of the present invention has a binding affinity for IL-17F of better than 10 nM. In one embodiment the antibody of the present invention has an affinity for IL-17F of better than 2 nM. In one embodiment the antibody of the present invention has an affinity for IL-17F of 1.75 nM.

Preferably the antibody molecule of the present invention has a binding affinity for IL-17A/F heterodimer of better than 10 nM. In one embodiment the antibody molecule of the present invention has a binding affinity for IL-17A/F heterodimer of better than 500 pM. In one embodiment the antibody molecule of the present invention has a binding affinity for IL-17A/F heterodimer of better than 150 pM. In one embodiment the antibody molecule of the present invention has a binding affinity for IL-17A/F heterodimer of 116 pM.

In one embodiment the antibody molecule of the present invention has a binding affinity for cynomolgus IL-17F of better than 2 nM. In one embodiment the antibody molecule of the present invention has a binding affinity for cynomolgus IL-17F of 1.03 nM.

It will be appreciated that the affinity of antibodies provided by the present invention may be altered using any suitable method known in the art. The present invention therefore also relates to variants of the antibody molecules of the present invention, which have an improved affinity for IL-17A and/or IL-17F. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

In one embodiment the antibody molecules of the present invention neutralise IL-17A and IL-17F activity, for example in the in vitro assays described in the Examples. In one embodiment the present invention provides a neutralising antibody having specificity for human IL-17A and IL-17F which is capable of inhibiting the activity of 0.8 nM human IL-17A by 50% at a concentration of less than 5 nM and the activity of 4.2 nM IL-17F by 50% at a concentration of less than 12 nM said inhibitory activity being measured on the IL-17A or IL-17F induced release of IL-6 from Hela cells. In one embodiment the concentration of antibody which inhibits IL-17A by 50% is less than 3 nM. In one embodiment the concentration of antibody which inhibits IL-17F by 50% is less than 11 nM. In one embodiment the human IL-17A and human IL-17F used in the assay are recombinant human IL-17A and IL-17F. In one embodiment the neutralising antibody is a humanised or fully human antibody.

If desired an antibody for use in the present invention may be conjugated to one or more effector molecule(s). It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO03031581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741, 900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Particular optional substituents which may be present on the above-mentioned synthetic polymers include one or more hydroxy, methyl or methoxy groups.

Particular examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Particular naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, preferably from 5000 to 40000 Da and more preferably from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Particularly preferred polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. Nos. 5,219,996; 5,667,425; WO98/25971). In one example the antibody molecule of the present invention is a modified Fab fragment wherein the modification is the addition to the C-terminal end of its heavy chain one or more amino acids to allow the attachment of an effector molecule. Preferably, the additional amino acids form a modified hinge region containing one or more cysteine residues to which the effector molecule may be attached. Multiple sites can be used to attach two or more PEG molecules.

Preferably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and Sun-Bio) and M-PEG-SPA (obtainable from Nektar, formerly Shearwater).

In one embodiment, the antibody is a modified Fab fragment which is PEGylated, i.e. has PEG (poly(ethyleneglycol)) covalently attached thereto, e.g. according to the method disclosed in EP 0948544 [see also "Poly(ethyleneglycol) Chemistry, Biotechnical and Biomedical Applications", 1992, J. Milton Harris (ed), Plenum Press, New York, "Poly (ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

In one embodiment, the present invention provides a neutralising antibody molecule having specificity for human IL-17A and human IL-17F, which is a modified Fab fragment having a heavy chain comprising the sequence given in SEQ ID NO:9 and a light chain comprising the sequence given in SEQ ID NO:7 and having at the C-terminal end of its heavy chain a modified hinge region containing at least one cysteine residue to which an effector molecule is attached. Preferably the effector molecule is PEG and is attached using the methods described in (WO98/25971 and WO2004072116) whereby a lysyl-maleimide group is attached to the cysteine residue at the C-terminal end of the heavy chain, and each amino group of the lysyl residue has covalently linked to it a methoxypoly(ethyleneglycol) residue having a molecular weight of about 20,000 Da. The total molecular weight of the PEG attached to the antibody is therefore approximately 40,000 Da.

In another example effector molecules may be attached to antibody fragments using the methods described in International patent applications WO2005/003169, WO2005/003170 and WO2005/003171.

The present invention also provides an isolated DNA sequence encoding the heavy and/or light chain(s) of an antibody molecule of the present invention. Preferably, the DNA sequence encodes the heavy or the light chain of an antibody molecule of the present invention. The DNA sequence of the present invention may comprise synthetic DNA, for instance produced by chemical processing, cDNA, genomic DNA or any combination thereof.

DNA sequences which encode an antibody molecule of the present invention can be obtained by methods well known to those skilled in the art. For example, DNA sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised on the basis of their known amino acid sequences.

Standard techniques of molecular biology may be used to prepare DNA sequences coding for the antibody molecule of the present invention. Desired DNA sequences may be synthesised completely or in part using oligonucleotide synthesis techniques. Site-directed mutagenesis and polymerase chain reaction (PCR) techniques may be used as appropriate.

Examples of suitable sequences are provided in SEQ ID NO:8; SEQ ID NO:10; SEQ ID NO:13; SEQ ID NO:14; SEQ ID NO:17 and SEQ ID NO:18. Nucleotides 1-57 in SEQ ID NO 18 and 1-60 in SEQ ID NO 14 encode the signal peptide sequence from mouse antibody B72.3 (Whittle et al., 1987, Protein Eng. 1 (6) 499-505.) which is cleaved to give a neutralising antibody molecule of the present invention.

The present invention also relates to a cloning or expression vector comprising one or more DNA sequences of the present invention. Accordingly, provided is a cloning or expression vector comprising one or more DNA sequences encoding an antibody of the present invention. Preferably, the cloning or expression vector comprises two DNA sequences, encoding the light chain and the heavy chain of the antibody molecule of the present invention, respectively. Preferably, a vector according to the present invention comprises the sequences given in SEQ ID NO:14 and SEQ ID NO:18. Nucleotides 1-57 in SEQ ID NO 18 and 1-60 in SEQ ID NO 14 encode the signal peptide sequence from mouse antibody B72.3 (residues 1-19 in SEQ ID NO: 16 and 1-20 in SEQ ID NO:12 respectively) which is most preferably cleaved to give a neutralising antibody molecule of the present invention.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding an antibody of the present invention. Any suitable host cell/vector system may be used for expression of the DNA sequences encoding the antibody molecule of the present invention. Bacterial, for example E. coli, and other microbial systems may be used or eukaryotic, for example mammalian, host cell expression systems may also be used. Suitable mammalian host cells include CHO, myeloma or hybridoma cells.

The present invention also provides a process for the production of an antibody molecule according to the present invention comprising culturing a host cell containing a vector of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

As the antibodies of the present invention are useful in the treatment and/or prophylaxis of a pathological condition, the present invention also provides a pharmaceutical or diagnostic composition comprising an antibody molecule of the present invention in combination with one or more of a pharmaceutically acceptable excipient, diluent or carrier. Accordingly, provided is the use of an antibody according to the present invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic composition comprising adding and mixing the antibody molecule of the present invention together with one or more of a pharmaceutically acceptable excipient, diluent or carrier.

The antibody molecule may be the sole active ingredient in the pharmaceutical or diagnostic composition or may be accompanied by other active ingredients including other antibody ingredients, for example anti-TNF, anti-IL-1β, anti-T cell, anti-IFNγ or anti-LPS antibodies, or non-antibody ingredients such as xanthines.

The pharmaceutical compositions preferably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 50 mg/kg, preferably 0.1 mg/kg to 20 mg/kg. Pharmaceutical compositions may be conveniently presented in unit dose forms containing a predetermined amount of an active agent of the invention per dose.

Compositions may be administered individually to a patient or may be administered in combination (e.g. simultaneously, sequentially or separately) with other agents, drugs or hormones.

The dose at which the antibody molecule of the present invention is administered depends on the nature of the condition to be treated, the extent of the inflammation present and on whether the antibody molecule is being used prophylactically or to treat an existing condition.

The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half life (e.g. 2 to 15 days) it may only be necessary to give a dosage once per day, once per week or even once every 1 or 2 months.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Preferred forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, it is preferred that the compositions are adapted for administration to human subjects.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO 98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

It is also envisaged that the antibody of the present invention will be administered by use of gene therapy. In order to achieve this, DNA sequences encoding the heavy and light chains of the antibody molecule under the control of appropriate DNA components are introduced into a patient such that the antibody chains are expressed from the DNA sequences and assembled in situ.

The present invention also provides an antibody molecule for use in the control of inflammatory diseases. Preferably, the antibody molecule can be used to reduce the inflammatory process or to prevent the inflammatory process.

The present invention also provides the antibody molecule of the present invention for use in the treatment or prophylaxis of a pathological disorder that is mediated by IL-17A and/or IL-17F or is associated with an increased level of IL-17A and/or IL-17F. Preferably, the pathological condition is selected from the group consisting of infections (viral, bacterial, fungal and parasitic), endotoxic shock associated with infection, arthritis, rheumatoid arthritis, asthma, pelvic inflammatory disease, Alzheimer's Disease, Crohn's disease, inflammatory bowel disease, Ulcerative colitis, Peyronie's Disease, coeliac disease, gallbladder disease, Pilonidal disease, peritonitis, psoriasis, vasculitis, surgical adhesions, stroke, Type I Diabetes, lyme arthritis, meningoencephalitis, immune mediated inflammatory disorders of the central and peripheral nervous system such as multiple sclerosis and Guillain-Barr syndrome, other autoimmune disorders, pancreatitis, trauma (surgery), graft-versus-host disease, transplant rejection, cancer (both solid tumours such as melanomas, hepatoblastomas, sarcomas, squamous cell carcinomas, transitional cell cancers, ovarian cancers and hematologic malignancies and in particular acute myelogenous leukaemia, chronic myelogenous leukemia, gastric cancer and colon cancer), heart disease including ischaemic diseases such as myocardial infarction as well as atherosclerosis, intravascular coagulation, bone resorption, osteoporosis, periodontitis and hypochlorhydia.

The present invention also provides an antibody molecule according to the present invention for use in the treatment or prophylaxis of pain.

The present invention further provides the use of an antibody molecule according to the present invention in the manufacture of a medicament for the treatment or prophylaxis of a pathological disorder that is mediated by IL-17A and/or IL-17F or associated with an increased level of IL-17A and/or IL-17F. Preferably the pathological disorder is rheumatoid arthritis or multiple sclerosis.

The present invention further provides the use of an antibody molecule according to the present invention in the manufacture of a medicament for the treatment or prophylaxis of pain.

An antibody molecule of the present invention may be utilised in any therapy where it is desired to reduce the effects of IL-17A and/or IL-17F in the human or animal body. IL-17 A and/or IL-17F may be circulating in the body or may be present in an undesirably high level localised at a particular site in the body, for example a site of inflammation.

An antibody molecule according to the present invention is preferably used for the control of inflammatory disease, autoimmune disease or cancer.

The present invention also provides a method of treating human or animal subjects suffering from or at risk of a disorder mediated by IL-17A and/or IL-17F, the method comprising administering to the subject an effective amount of an antibody molecule of the present invention.

An antibody molecule according to the present invention may also be used in diagnosis, for example in the in vivo diagnosis and imaging of disease states involving IL-17A and/or IL-17F.

(QIAGEN, catalogue No. 12165). DNA sequencing reactions were performed using the ABI Prism Big Dye terminator sequencing kit (catalogue No. 4304149) and run on an ABI 3100 automated sequencer (Applied Biosystems). Data was analysed using the program AutoAssembler (Applied Biosystems). Oligonucleotides were obtained from Invitrogen. The concentration of IgG was determined using IgG assembly ELISA.

IL-17 Isoforms

Recombinant IL-17A and IL-17F were purchased from R&D Systems.

Recombinant IL-17A/F heterodimer was produced by linking IL-17A and IL-17F using a GS linker. The heterodimer had the following sequence (SEQ ID NO:19)

```
MGITIPRNPGCPNSEDKNFPRTVMVNLNIHNRNTNTNPKRSSDYYNRST

SPWNLHRNEDPERYPSVIWEAKCRHLGCINADGNVDYHMNSVPIQQEIL

VLRREPPHCPNSFRLEKILVSVGCTCVTPIVHHVAGGGGSGGGGSGGGG

SGGGGSRKIPKVGHTFFQKPESCPPVPGGSMKLDIGIINENQRVSMSRN

IESRSTSPWNYTVTWDPNRYPSEVVQAQCRNLGCINAQGKEDISMNSVP

IQQETLVVRRKHQGCSVSFQLEKVLVTVGCTCVTPVIHHVQ
```

Recombinant cynomolgus IL-17F (SEQ ID NO:20)

```
MRKIPKVGHTFFQKPESCPPVPEGSMKLDTGIINENQRVSMSRNIESRSTSPWNYTVTWDPN

RYPSEVVQAQCKHLGCINAQGKEDISMNSVPIQQETLVLRRKHQGCSVSFQLEKVLVTVGCT

CVTPVIHHVQ
```

The present invention is further described by way of illustration only in the following examples, which refer to the accompanying Figures, in which:

FIG. 1 a) Light chain V region of antibody CA028_0496 (SEQ ID NO:7)
b) Heavy chain V region of antibody CA028_0496 (SEQ ID NO:9)
c) CDRH1 (SEQ ID NO:1), CDRH2 (SEQ ID NO:2), CDRH3 (SEQ ID NO:3), CDRL1 (SEQ ID NO:4), CDRL2 (SEQ ID NO:5), CDRL3 (SEQ ID NO:6) of antibody CA028_496.
d) Light chain of antibody CA028_496 (SEQ ID NO:11).
e) Heavy chain of antibody CA028496 (SEQ ID NO:15).
f) DNA encoding light chain of antibody CA028_496 including signal sequence (SEQ ID NO:14).
g) DNA encoding heavy chain of antibody CA028_496 including signal sequence (SEQ ID NO:18)

Figure 2B:
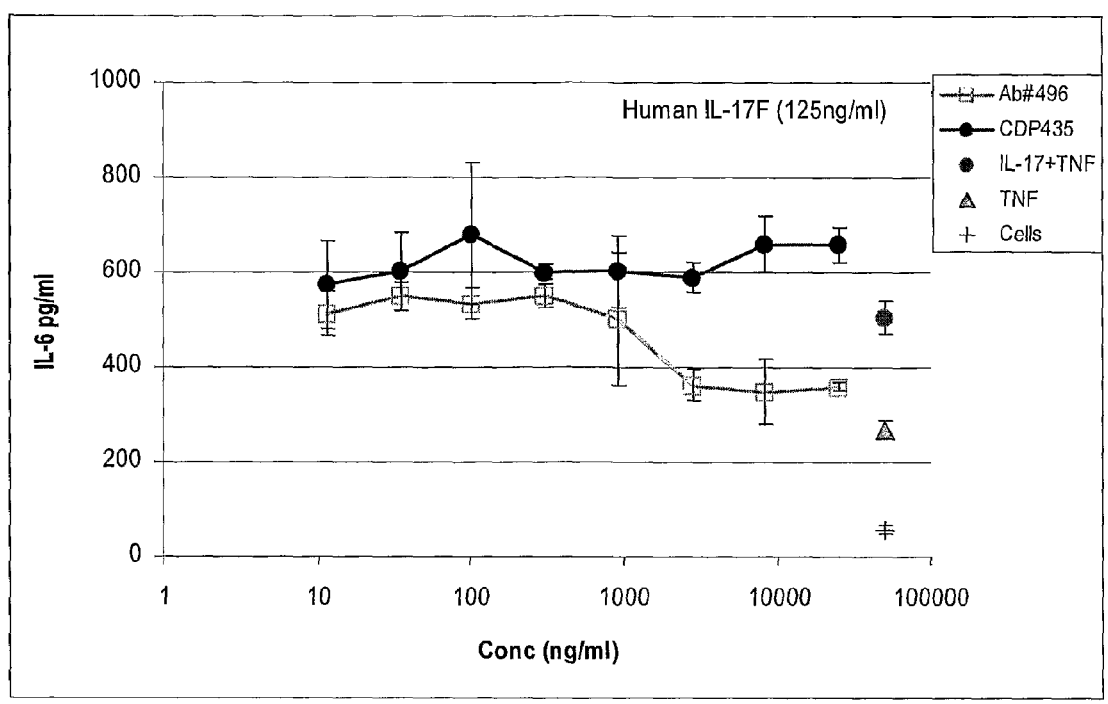

FIG. 2 a) The effect of antibody CA028_0496 (designated Ab#496 in legend) on human IL-17 induced IL-6 production from Hela cells. b) The effect of antibody CA028_0496 (designated Ab#496 in legend) on human IL-17F induced IL-6 production from Hela cells

DNA MANIPULATIONS AND GENERAL METHODS

*E. coli* strain INVαF' (Invitrogen) was used for transformation and routine culture growth. DNA restriction and modification enzymes were obtained from Roche Diagnostics Ltd. and New England Biolabs. Plasmid preparations were performed using Maxi Plasmid purification kits The DNA sequence encoding IL-17A/F heterodimer was chemically synthesised by Entelechon GmbH and was subcloned into pET43.1a at the NdeI/XhoI sites. The DNA sequence encoding cyno L-17F was amplified by PCR using primers that introduced NdeI and XhoI restriction sites. The PCR products were ligated into pCR4Blunt-TOPO and sequence verified before digestion and ligation into pET43.1a at the NdeI/XhoI sites.

pET43.1a DNA encoding IL-17 isoforms was used to transfect BL21(DE3) cells and selected carbenicillin-resistant clones were grown at 37° C. overnight in 2TY broth containing 2% glucose and 50 µg/ml carbenicillin. The cultures were then diluted and grown in the same medium to an $OD_{600}$ of 0.5-0.7, induced with 1 mM IPTG and grown at 37° C. for a further 4-5 hours.

Cells were harvested by centrifugation and inclusion bodies prepared from the cells. Inclusion bodies were solubilised in 50 mM Tris-HCl, 5M guanidinium hydrochloride, 50 mM NaCl, 1 mM EDTA, 2 mM reduced glutathione, 0.2 mM oxidised glutathione, pH 8.5. IL-17 protein was refolded by dropwise addition of the solubilised protein to the above buffer without guanidinium hydrochloride, with vigorous stirring. The final volume was chosen such that the final protein concentration was no more than 0.1 mg/ml.

The refolded protein solution was concentrated if required, before buffer exchange with 10 mM MES pH6. The protein was then applied to a column of Sepharose SP HP equilibrated with 20 mM MES pH6. Protein was eluted with a linear gradient of 0-500 mM NaCl in MES pH6 over 10 column volumes. For IL-17F the gradient was extended to 600 mM NaCl. In order to further purify IL-17, the relevant fraction from the Sepharose SP HP column were pooled, concentrated and diluted with 20 mM CAPSO (pH10) and applied to a Mono Q column equilibrated with 20 mM CAPSO. Protein was eluted with a linear gradient of 0-250 mM NaCl in 20 mM CAPSO over 20 column volumes. Fractions containing IL-17 were pooled and neutralised using 1M MES pH6.

EXAMPLE 1

Production of a Neutralising Anti-IL-17 Antibody

Female Sprague Dawly rats were immunised with recombinant human IL-17 (purchased from R & D systems). Rats received four immunisations of 20 µg IL-17 in 1000 Freund's adjuvant. Antibody 225 which binds human IL-17 was isolated using the methods described in WO04/051268. Genes for the heavy chain variable domain (VH) and light chain variable domain (VL) of antibody 225 were isolated and sequenced following cloning via reverse transcription PCR.

A series of humanised VL and VH regions were designed using human V-region acceptor frameworks and by varying the number of donor residues in the framework regions. Eight grafted VL regions (gL1-8) and 9 grafted VH regions (gH1-9) were designed and genes were built by oligonucleotide assembly and PCR mutagenesis.

The light chain grafted sequences were sub-cloned into the human light chain expression vector pKH10.1 which contains the DNA encoding the human C-Kappa constant region (Km3 allotype). The heavy chain grafted sequences were subcloned into the human gamma-4 expression vector pVhg4P FL, which contains the DNA encoding the human gamma-4 constant region containing the hinge stabilising mutation S241P (Angal et al., supra). Plasmids were co-transfected into CHO cells and the antibodies produced screened for activity in IL-17 binding and neutralisation assays. Transfections of CHO cells were performed using the Lipofectamine™ 2000 procedure according to manufacturer's instructions (InVitrogen, catalogue No. 11668).

The most optimal graft based on expression, affinty and neutralisation potency (gL7gH9) was selected and named CA028_0496. The V region sequences of this antibody are shown in FIGS. 1 (a) and (b) and in SEQ ID NOs: 7 and 9 for the light chain (gL7) and heavy chains (gH9) respectively.

The heavy chain acceptor framework is the human germline sequence VH3 1-3 3-07 with framework 4 coming from this portion of the human JH-region germline JH4. The light chain acceptor framework is the human germline sequence VK1 2-1-(1) L4, with framework 4 coming from this portion of the human JK-region germline JK1.

EXAMPLE 2

Antibody CA028_0496 Neutralises IL-17 and IL-17F and IL-17A/F Heterodimer

Hela Cells

The potency of antibody CA028_0496 against human recombinant IL-17 and human recombinant IL-17F in Hela cells was tested and compared to antibody CDP435 (WO06/054059). Hela cells were obtained from the cell bank at ATCC (ATCC CCL-2). Cells were grown in Dulbecco's modified Eagle's medium (DMEM) supplemented with 10% foetal calf serum, penicillin, gentamycin and glutamine. $1 \times 10^4$ cells were plated out into 96 well flat bottomed tissue culture plates. Cells were incubated overnight and washed once in assay buffer. Either human IL-17A (25 ng ml$^{-1}$) or human IL-17F (125 ng ml$^{-1}$) was incubated in the presence of a fixed concentration of human TNF-α this mixture was preincubated with antibody CA028_0496 or antibody CDP435. Cytokine plus antibody was then added to the Hela cells which were incubated overnight. The production of IL-6 in the cell culture supernatant was proportionate to the amount of IL-17A/IL-17F added to the cells. Human IL-6 levels were measured by ELISA and quantified by comparison with known standard concentrations of human IL-6.

The data (FIGS. 2a and 2b) indicates that antibody CA028_0496 potently neutralised human recombinant IL-17A and also had some activity against human IL-17F. The data from these experiments indicated that antibody CA028_0496 gave an IC$_{50}$ of 43/ng/ml against human recombinant IL-17 (25 ng ml$^{-1}$) and 1477 ng/ml against recombinant IL-17F (125 ng ml$^{-1}$).

Accordingly, antibody CA028_0496 gave an IC50 of 0.29M against human recombinant IL-17 (0.78 nM) and 10.18 nM against human recombinant IL-17F (4.16 nM) in this assay (calculation based on per IgG assuming a molecular weight of 145,000 as an average IgG4 and assuming that IL-17A and IL-17F are dimers).

Human Microglia Cells

Human microglia cells (TCS Cellworks) were plated out in a flat bottom 96-well plate at 5,000 cells per well in a total volume of 100 µl and left for 24 hours to attach to the plastic. At this time titrations (5, 1, 0.2 and 0.04 µg/ml) of human recombinant IL-17A, human recombinant IL-17F, cynomolgus recombinant IL-17F and human recombinant IL-17A/F heterodimer in the presence and absence of 10 ng/ml human recombinant TNFα were added to wells in triplicate. Control wells contained no stimulation, IL-17A alone (100 ng/ml), TNFα alone and IL-17A and TNFα together. All cytokines were added in a total volume of 110 µl/well, making the total well volume 210 µl. In experiments involving antibodies, cells were plated out in the same way. After 24 hours antibodies and cytokines were added at the same time to give the stated final concentrations in a total final volume of 200 µl.

After a further 24 hours incubation at 37° C., supernatants were harvested and frozen at −20° C. until analysis. For analysis, supernatants were diluted ⅒ and measured for IL-6 using a human IL-6 MSD kit, according to manufacturer's instructions.

All isoforms of IL-17 tested were found to be active in the assay, particularly in the presence of TNFα.

The potency of antibody CA028_0496 against human recombinant IL-17A and human recombinant IL-17F, cynomolgus recombinant IL-17F and human recombinant IL-17A/F heterodimer in human microglia cells was tested in the presence of TNFα and compared to a control antibody and an IL-17A specific antibody using the method described above.

The control antibody had no effect on the activity of any of the cytokines tested. Antibody CA028_0496 had inhibitory activity against all three cytokines IL-17, IL-17F and IL-17A/F, including cynomolgus IL-17F while the IL-17A specific antibody only had inhibitory activity against IL-17A and IL-17A/F heterodimer.

EXAMPLE 3

Affinity of Antibody CA028_0496 (Human IgG4 Constant Regions) for IL-17A and IL-17F BIA (Biamolecular Interaction Analysis) was performed using a Biacore 3000 (Biacore AB). All experiments were performed at 25° C. Affinipure Fc Fragment goat anti-human IgG, Fc fragment specific (Jackson ImmunoResearch) was immobilised on a CM5 Sensor Chip via amine coupling chemistry to a capture level of ≈6000 response units (RUs). HBS-EP buffer (10 mM HEPES pH 7.4, 0.15 M NaCl, 3 mM EDTA, 0.005% Surfactant P20, Biacore AB) was used as the running buffer with a flow rate of 10 µl/min. A 10 µl injection of antibody CA028_0496 (1.81 mg/ml) was used for capture by the immobilised anti-human IgG-Fc. Human IL-17A and IL-17 isoforms were titrated over the captured CA028_0496 at doubling dilutions from 50 nM to sub nM at a flow rate of 30 µL/min. The surface was regenerated by a 30 µL injections of 40 mM HCl, followed by one 5 µL injection of 5 mM NaOH.

Background subtraction binding curves were double referenced and analysed using the BIAevaluation software (version 3.2) following standard procedures. Kinetic parameters were determined from the fitting algorithm.

The affinity value determined for antibody CA028_0496 binding IL-17A was 16 pM and 1750 pM for IL-17F. Antibody CA028_0496 did not bind to the other IL-17 isoforms (IL-17 B, C, D and E). Antibody CA028_0496 therefore specifically binds IL-17A and IL-17F.

EXAMPLE 4

Affinity of Antibody CA028_0496 (Murine IgG1 Constant Regions) for IL-17A, Cynomolgus IL-17F and IL-17A/F Heterodimer BIA (Biamolecular Interaction Analysis) was performed using a Biacore 3000 (Biacore AB).

All experiments were performed at 25° C. Affinipure F(ab')$_2$ fragment goat anti-mouse IgG, Fc fragment specific (Jackson ImmunoResearch) was immobilised on a CM5 Sensor Chip (Biacore AB) via amine coupling chemistry to a capture level of ≈6000 response units (RUs). HBS-EP buffer (10 mM HEPES pH 7.4, 0.15 M NaCl, 3 mM EDTA, 0.005% Surfactant P20, Biacore AB) was used as the running buffer with a flow rate of 10 µL/min. A 10 µL injection of antibody CA028_0496 at 4 ug/mL was used for capture by the immobilised anti-mouse IgG, Fc. Human IL-17A, cyno IL-17F and heterodimerA/F were titrated over the captured CA028_0496 at doubling dilutions from 25 nM to sub nM at a flow rate of 30 µL/min. The surface was regenerated at a flowrate of 10 uL/min by a 10 µL injection of 40 mM HCl, followed by a 5 µL injection of 5 mM NaOH.

Double referenced background subtracted binding curves were analysed using the BIAevaluation software (version 3.2) following standard procedures. Kinetic parameters were determined from the fitting algorithm.

Antibody CA028_0496 had an affinity of 21 pM for IL-17A, 116 pM for IL-17A/F heterodimer and 1030 pM for cynomolgus IL-17F.

It will of course be understood that the present invention has been described by way of example only, is in no way meant to be limiting, and that modifications of detail can be made within the scope of the claims hereinafter. Preferred features of each embodiment of the invention are as for each of the other embodiments mutatis mutandis. All publications, including but not limited to patents and patent applications, cited in this specification are herein incorporated by reference as if each individual publication were specifically and individually indicated to be incorporated by reference herein as though fully set forth.

The invention claimed is:

1. An isolated DNA molecule encoding a neutralising antibody which binds human IL-17A and human IL-17F, wherein the variable domain of the heavy chain comprises the sequence given in SEQ ID NO: 1 for CDR-H1, the sequence given in SEQ ID NO: 2 for CDR-H2 and the sequence given in SEQ ID NO: 3 for CDR-H3, and wherein the variable domain of the light chain comprises the sequence given in SEQ ID NO: 4 for CDR-L1, the sequence given in SEQ ID NO: 5 for CDR-L2 and the sequence given in SEQ ID NO: 6 for CDR-L3, or an antigen-binding fragment thereof.

2. A cloning or expression vector comprising the DNA molecule according to claim 1.

3. The vector according to claim 2, wherein the vector comprises the sequences given in SEQ ID NO: 14 and SEQ ID NO: 18.

4. An isolated host cell comprising the vector according to claim 3.

5. A process for the production of an antibody encoded by the DNA molecule in the vector of the isolated host cell of claim 4, comprising culturing the isolated host cell under conditions suitable for expression of the antibody, and isolating the antibody.

6. An isolated host cell comprising the vector according to claim 2.

7. A process for the production of an antibody encoded by the DNA molecule in the vector of the isolated host cell of claim 6, comprising culturing the isolated host cell under conditions suitable for expression of the antibody, and isolating the antibody.

8. An isolated DNA molecule encoding a neutralising antibody which binds human IL-17A and human IL-17F, wherein the heavy chain comprises the sequence given in SEQ ID NO: 9 and wherein the light chain comprises the sequence given in SEQ ID NO: 7, or an antigen-binding fragment thereof.

9. A cloning or expression vector comprising the DNA molecule according to claim 8.

10. An isolated host cell comprising the vector according to claim 9.

11. A process for the production of an antibody encoded by the DNA molecule in the vector of the isolated host cell of claim 10, comprising culturing the isolated host cell under conditions suitable for expression of the antibody, and isolating the antibody.

12. An isolated DNA molecule encoding a neutralising antibody which binds human IL-17A and human IL-17F, wherein the heavy chain comprises the sequence given in SEQ ID NO: 15 and wherein the light chain comprises the sequence given in SEQ ID NO: 11, or an antigen-binding fragment thereof.

13. A cloning or expression vector comprising the DNA molecule according to claim 12.

14. An isolated host cell comprising the vector according to claim 13.

15. A process for the production of an antibody encoded by the DNA molecule in the vector of the isolated host cell of claim 14, comprising culturing the isolated host cell under conditions suitable for expression of the antibody, and isolating the antibody.

16. An isolated DNA molecule encoding a neutralising antibody which binds human IL-17A and human IL-17F, wherein the heavy chain comprises the sequence given in SEQ ID NO: 9.

17. An isolated DNA molecule encoding a neutralising antibody which binds human IL-17A and human IL-17F, wherein the light chain comprises the sequence given in SEQ ID NO: 7.

* * * * *